United States Patent [19]

Howe et al.

[11] 4,380,465
[45] Apr. 19, 1983

[54] 5-ARYL-4-ISOTHIAZOLECARBOXYLIC ACIDS AND DERIVATIVES

[75] Inventors: Robert K. Howe, Bridgeton; Len F. Lee, St. Charles, both of Mo.

[73] Assignee: Monsanto Company, St. Louis, Mo.

[21] Appl. No.: 197,833

[22] Filed: Oct. 17, 1980

Related U.S. Application Data

[63] Continuation-in-part of Ser. No. 33,779, Apr. 27, 1979, abandoned.

[51] Int. Cl.³ .................... A01N 43/02; A01N 37/18
[52] U.S. Cl. .......................................... 71/90; 71/118; 71/DIG. 1
[58] Field of Search .................................. 71/90, 118

[56] References Cited

U.S. PATENT DOCUMENTS

| | | | |
|---|---|---|---|
| 3,131,509 | 5/1964 | Hoffmann | 47/1 |
| 3,155,678 | 11/1964 | Hatchard | 260/302 |
| 3,498,995 | 3/1970 | McGregor et al. | 260/302 |
| 3,551,440 | 12/1970 | Naito et al. | 260/302 |
| 3,663,200 | 5/1972 | Olin | 71/118 |
| 3,989,503 | 11/1976 | Pallos et al. | 71/88 |
| 4,115,095 | 9/1978 | Franz et al. | 71/90 |
| 4,120,861 | 10/1978 | Brouwer et al. | 548/136 |
| 4,135,910 | 1/1979 | Howe | 71/76 |
| 4,144,047 | 3/1979 | Franz et al. | 71/90 |
| 4,187,099 | 2/1980 | Franz et al. | 71/90 |
| 4,279,636 | 7/1981 | Hoffmann et al. | 71/90 |

OTHER PUBLICATIONS

Gotthardt, "Isothiazole ans 1.3.2–etc.,"(1971) Chem. Ber 105 pp. 196–202 (1972).

*Primary Examiner*—Glennon H. Hollrah
*Attorney, Agent, or Firm*—Stanley M. Tarter; Donald W. Peterson

[57] ABSTRACT

5-Aryl-4-isothiazolecarboxylic acids have been found to reduce herbicidal injury of rice plants due to the application of 2-chloro-2',6'-diethyl-N-(butoxymethyl)-acetanilide.

9 Claims, No Drawings

5-ARYL-4-ISOTHIAZOLECARBOXYLIC ACIDS AND DERIVATIVES

This is a Continuation-In-Part of Ser. No. 33,779, filed Apr. 27, 1979 now abandoned.

This invention relates to 5-aryl-4-isothiazolecarboxylic acids and derivatives thereof which are useful in compositions and methods for reducing herbicidal injury. More specifically, the invention relates to compositions and methods for reducing injury to crop plants by herbicides which comprises treating the crop plant locus or the seed of the crop plant with an effective amount of a 5-aryl-4-isothiazolecarboxylic acid or derivative thereof.

Herbicides are very useful for controlling certain weeds in the presence of growing crops. However many herbicides tend to injure crop plants, slowing growth and development at rates necessary to stunt or kill the weeds. For example, acetanilide herbicides can injure direct seeded rice. Obviously, a safening agent consisting of a composition that could be used to treat the seed of the crop plant, the crop plant locus or the crop plant itself, resulting in a reduction of injury due to application of the herbicide without a corresponding reduction of herbicidal action on the weed would be quite beneficial.

In accordance with the novel aspects of the present invention, injury to rice plants, due to application of 2-chloro-2',6'-diethyl-N-(butoxymethyl)acetanilide (hereinafter referred to by its common name, butachlor), may be reduced without a corresponding reduction in injury to the weeds by application to the crop plant locus or the seed of the crop plant prior to planting of a safening effective amount of a safening agent comprising a 5-aryl-4-isothiazolecarboxylic acid or derivative thereof having the formula

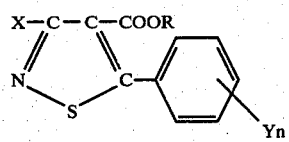

wherein X is hydrogen or halogen, R is hydrogen, lower alkyl or agriculturally acceptable cations, Y is halogen, lower alkyl or trifluoromethyl and n is 0, 1 or 2.

As used herein the term "lower alkyl" is understood to include alkyl groups having up to five carbon atoms, inclusive. Said alkyl groups are understood to include branched and unbranched groups.

The term "agriculturally acceptable cations" is understood to mean those cations that are commonly used to form the salt of the free acid. Such cations include, but are not limited to, alkali metal, alkaline earth, substituted amine and ammonium cations.

Preferably, "halogens" include chloro, bromo and fluoro, especially chloro.

The safening agents of the foregoing formula may be prepared from 5-aryl-4-isothiazolecarbonitriles which may be prepared in accordance with an article written by Nakagawa et al, Tetrahedron Letters No. 42, pp. 3719-3722, 1970. Additionally, it should be noted that preparation of the 5-aryl-4-isothiazolecarboxylic acids have been taught by Gotthardt, Chem. Ber. Vol. 105 (1972) page 196. For purposes of clarity the following examples are presented illustrating the procedure utilized to prepare the 5-aryl-4-isothiazolecarboxylic acids of the present invention and are not intended to be a limitation with respect to the scope of the invention.

EXAMPLE 1

Preparation of 3-chloro-5-phenyl-4-isothiazolecarboxylic acid

A mixture of 2.20 g (10 mole) of 3-chloro-5-phenyl-4-isothiazolecarbonitrile and 10 ml of concentrated sulfuric acid was heated at 130°-140° for 3 hours and cooled with an ice bath. A solution of 1.0 g (14.5 mole) of sodium nitrite in 5 ml of water was added dropwise. The addition of sodium nitrite solution was adjusted so that the temperature did not exceed 30°. After complete addition of the sodium nitrite solution, the mixture was poured into 200 ml of water, and the mixture was heated at 50° for ½ hour and cooled. The aqueous solution was extracted with ether (24.50 ml). The ether extract was extracted with 50 ml of 10% sodium hydroxide (2 times). The extract was made acidic with 50 ml of concentrated HCl (a precipitate formed) and was extracted twice with 50 ml of ether. The ether solution was dried (MgSO$_4$) and concentrated to give 1.8 g (75%) of tan needles, mp 166.5°-168°, which was recrystallized from hexane: ether to give 1.7 g (71%) of the desired product as yellow needles. mp 167°-169°.

Anal. Calc'd for C$_{10}$H$_6$ClNO$_2$S: C, 50.11; H, 2.82; N, 5.85; Cl, 14.9

Found: C, 50.19; H, 2.53; N, 5.88; Cl, 14.3

EXAMPLE 2

Preparation of 3-chloro-5-(m-trifluoromethylphenyl)-4-isothiazolecarboxylic acid To a solution of 50.0 g (0.287 mole) of m-trifluoromethylbenzaldehyde, 25.0 g (0.378 mole) of malononitrile, and 500 ml of n-butanol was added 15 drops of piperidine. The mixture was stirred for 16 hours, and the white precipitate was collected and washed with ethanol to give 34 g (53%) of white prisms, mp 82°-83°. Concentration of the mother liquid down to 100 ml and cooling gave an additional 3 g of prisms, mp 82°-85°. This material (3 g) was recrystallized from ethanol to give an additional 2.0 g of m-trifluoromethylbenzylidinemalononitrile, mp 82°-83°. A mixture of 30.8 g (0.139 ml) of m-trifluoromethylbenzylidinemalononitrile, 46.92 g (0.348 mole) of S$_2$Cl$_2$, and 1.66 g (0.021 mole) of pyridine was stirred at 140° to 150° for 5 hours and poured onto 500 ml of ice water. The precipitate was collected and dissolved in hot ethanol (500 ml). The insoluble sulfur was removed by filtration, and the filtrant was concentrated to 300 ml and cooled to room temperature. The product obtained as yellow needles (35 g, mp 102.5°-105°) was 3-chloro-5-(m-trifluoromethylphenyl)-4-isothiazolecarbonitrile. The yellow needles were recrystallized from ethanol to give 30.8 g (77%), mp 103.5°-105°, of yellow needles. A portion of the needles was recrystallized again, mp 103.5°-105°. However, recrystallization of the carbonitrile from hexane gave 25 g of material with mp 105°-106°. The mixture of 6.4 g (0.0222 mole) of 3-chloro-5-(m-trifluoromethylphenyl)-4-isothiazolecarbonitrile in 30 ml of concentrated sulfuric acid was heated in a steam bath for 45 minutes and poured into 300 ml of ice water. The yellow precipitate was filtered and dissolved in a mixture of 30 ml of methanol and 200 ml of ether. The solution was extracted with 10% sodium hydroxide solution (50 ml), dried (MgSO$_4$) and concentrated under reduced pressure, and the residual solid was crystallized from methanol-water to give 5.25 g (77%) of 3-chloro-5-(m-trifluoromethylphenyl)-4-isothiazolecarboxamide as yellow needles, mp 143°–147°. A portion of this material (0.5 g) was further recrystallized from methanol-water to give mp 145°–146°. To a cold (5°) solution of 1.0 g (3.26 mole) of 3-chloro-5-(m-trifluoromethyl-phenyl)-4-isothiazolecarboxamide in 20 ml of concentrated sulfuric acid was added a solution of 2.0 g (14.5 mole) of sodium nitrite in 5 ml of water dropwise to maintain a temperature below 30°. After complete addition of the sodium nitrite solution the reaction mixture was stirred at room temperature for 1 hour and then in a steam bath for 30 minutes and hydrolyzed with 200 ml of water. The precipitate was extracted with 50 ml of ether (2 times). The ether solution was extracted twice with 50 ml of 10% sodium hydroxide solution. The basic extracts were made acidic with 30 ml of concentrated HCl, and the resulting precipitate was filtered to give 0.2 g (20%) of the desired acid mp 159°–161°. Further recrystallization from ethanol-water gave mp 159°–161°.

Anal. Calc'd for $C_{11}H_5ClF_3NO_2S$: C, 42.94; H, 1.64; Cl, 11.52; N, 4.55; S, 10.42

Found: C, 42.96; H, 1.66; Cl, 11.67; N, 4.63; S, 10.59

EXAMPLE 3

Utilizing a procedure similar to that of Example 2, 3-chloro-5-(p-chlorophenyl)-4-isothiazolecarboxylic acid, mp 163°–167°, was prepared and recrystallized from ethanol-water and then from toluene to give 3.0 g of a solid mp 166°–168.5°.

Anal. Calc'd for $C_{10}H_5Cl_2NO_2S$: C, 43.81; H, 1.84; N, 5.11; Cl, 25.87

Found: C, 43.77; H, 1.86; N, 5.15; Cl, 25.78

EXAMPLE 4

Utilizing a procedure similar to that of Example 2, 3-chloro-5-(2',4'-dichlorophenyl)-4-isothiazolecarboxylic acid was prepared, mp 185°–191°.

Anal. Calc'd for $C_{10}H_4Cl_3NO_3S$: C, 38.92; H, 1.30; N, 4.54; Cl, 34.48

Found: C, 38.89; H, 1.31; N, 4.55; Cl, 34.39

In all of the above examples, all temperatures are expressed in degrees Centigrade.

The above examples illustrate the preparation of 3-halo-5-aryl-4-isothiazolecarboxylic acids by reacting a benzaldehyde with a malononitrile to form a benzylidinemalononitrile to which may be added sulfur monochloride giving 3-halo-5-aryl-4-isothiazolecarbonitrile. Acid hydrolysis of the isothiazolecarbonitrile yields 3-halo-5-aryl-4-isothiazolecarboxamide. The amide may be converted to the acid by reaction with sodium nitrite an an acid, e.g. sulfuric acid.

5-aryl-4-isothiazolecarboxylic acids which are unsubstituted in the 3-position may be prepared by thermolysis of the 3,4-dicarboxylic acid prepared by Gotthardt, Chem. Ber. Vol. 105 (1972) pp 196 as follows:

EXAMPLE 5

0.65 g of 5-phenyl-3,4-isothiazoledicarboxylic acid was heated at 170°–175° for 10 minutes and cooled. Purification in accordance with known techniques in the literature gave 0.30 g of yellow solid mp 182°–183° C.

Esters and salts may be prepared from the free acid utilizing standard procedures well known to those skilled in the art.

The amount of 5-aryl-4-isothiazolecarboxylic acid and derivatives of the foregoing formula (hereinafter referred to as "safening agent") employed in the method and compositions of the invention will vary depending upon the rate of application of the herbicide as well as the manner of application of the safening agent. In each instance, the amount employed is a safening effective amount, i.e., the amount which reduces crop injury by the herbicide.

The safening agent may be applied to the plant locus in a mixture with the herbicide, sequentially or it may be applied directly to the seed of the crop plant. By application to the "plant locus" is meant application to the plant growing medium, such as the soil, as well as the seeds, emerging seedlings, roots, stems, leaves, flowers, fruit or other plant parts.

The amount of butachlor employed is well within the skill of the art and is disclosed in U.S. Pat. Nos. 3,442,945 and 3,547,620.

To illustrate the effectiveness of the 5-aryl-4-thiazolecarboxylic acids and derivatives thereof, the following examples are presented. These examples are presented merely as being illustrative of the novel aspects of the invention and are not intended to be a limitation as to the scope thereof.

EXAMPLE 6

A good grade of top soil is placed in a container and compacted to a depth of approximately 1.27 cm from the top of said container. A predetermined number of rice seeds are placed on top of the soil. A quantity of soil sufficient to substantially fill the container is measured and placed in a second container. A measured quantity of the safening agent dispersed or dissolved in a suitable carrier is applied to the soil in the second container. A measured quantity of the butachlor dispersed or dissolved in a suitable carrier is then sprayed on the soil already treated with the safening agent. The soil containing the safening agent and herbicide is thoroughly mixed. This mixing is sometimes referred to as incorporation of the herbicide and safening agent into the soil. The mixing or incorporation provides a substantially uniform distribution of the safening agent and herbicide throughout the soil. The seeds are covered with the soil containing the safening agent and acetamide herbicide and the pots are leveled. The pots are then placed on a sand bench in the greenhouse and watered from below as needed. The plants are observed at the end of approximately 21 days and the results in terms of percent inhibition of each seed lot are recorded. For each test series, a pot is also prepared containing no herbicide and no safening agent as a control. Additionally, for each test, pots are prepared with soil covering the seed containing no herbicide and only the measured amount of safening agent being incorporated into the soil covering the seeds to ascertain any herbicidal effect of the safening agent alone. For each series of tests, the herbicidal effect of the herbicide is observed from pots treated with the same quantity of herbicide alone. The "safening effect" is determined by adding the herbicidal effect of the herbicide when applied alone to the herbicidal effect of the safening agent when applied alone (in no instance, however, will this sum be greater than 100) and subtracting from that the herbicidal effect obtained when both the herbicide and safening agent are incorporated into the soil as discussed above.

Table I summarizes the results obtained when the compounds of the invention were tested in accordance with the procedure of Example 6.

TABLE I

| RATE OF HERBICIDE (kg/h) | SAFENING AGENT (Example No.) | RATE OF SAFENING AGENT (kg/h) | SAFENING EFFECT |
|---|---|---|---|
| 4.48 | 1 | 8.96 | 60 |
| 4.48 | 2 | 8.96 | 25 |
| 6.72 | 3 | 8.96 | 30 |
| 6.72 | 4 | 8.96 | 60 |
| 4.48 | 5 | 8.96 | 43 |

EXAMPLE 7

A good grade of top soil is placed in a plastic pot. A measured quantity of the safening agent dispersed or dissolved in a suitable carrier is sprayed on the soil surface. A measured quantity of butachlor herbicide dissolved in a solvent is sprayed on the soil surface. Pre-soaked rice is seeded into the pots that were previously flooded with water and the water level lowered below the soil surface for one week. The pots are flooded at least up to the soil surface for the duration of the test. The plants are observed at the end of approximately 21 days and the results in terms of the percent inhibition of rice is recorded. As in Example 6, for each test pots are prepared containing soil treated only with butachlor. For each test, pots are also prepared containing soil treated only with the safening agent. Pots are also prepared in which the soil is not treated with either the herbicide or the safening agent.

Tables II and III summarize the results obtained when the compounds of the invention were tested in accordance with the procedure of Example 7.

TABLE II

| RATE OF HERBICIDE (kg/h) | SAFENING AGENT (Example No.) | RATE OF SAFENING AGENT (kg/h) | % INHIBITION OF RICE |
|---|---|---|---|
| 0.035 | — | — | 5 |
| 0.14 | — | — | 78 |
| 0.56 | — | — | 99 |
| — | 1 | 1.12 | 0 |
| 0.035 | 1 | 1.12 | 0 |
| 0.14 | 1 | 1.12 | 0 |
| 0.56 | 1 | 1.12 | 50 |

TABLE III

| RATE OF HERBICIDE (kg/h) | SAFENING AGENT | RATE OF SAFENING AGENT (kg/h) | % INHIBITION OF RICE |
|---|---|---|---|
| 0.035 | — | — | 4 |
| 0.14 | — | — | 64 |
| 0.56 | — | — | 99 |
| — | 5 | 1.12 | 0 |
| 0.035 | 5 | 1.12 | 3 |
| 0.14 | 5 | 1.12 | 10 |
| 0.56 | 5 | 1.12 | 90 |

EXAMPLE 8

A good grade of top soil is placed in a plastic pot. A measured quantity of the safening agent dispersed or dissolved in a suitable carrier is sprayed on the soil surface. A measured quantity of butachlor herbicide dissolved in a solvent is sprayed on the soil surface. Barnyard grass and rice are seeded into pots and watered from below. The plants are observed at the end of 19 days and the results in terms of the percent inhibition of barnyard grass and rice are recorded. As in Example 6, for each test pots are prepared containing soil treated only with butachlor. For each test, pots are also prepared containing soil treated only with the safening agent. Pots are also prepared in which the soil is not treated with either the herbicide or the safening agent.

Table IV summarizes the results obtained when the compounds of the invention were tested in accordance with the procedure of Example 8.

TABLE IV

| Rate of Herbicide (kg/h) | Safening Agent (Ex. No.) | Rate of Safening Agent | Percent Inhibition of Barnyard Grass | Percent Inhibition of Rice |
|---|---|---|---|---|
| 2.24 | | | 100 | 90 |
| 4.48 | | | 100 | 96 |
| 8.96 | | | 100 | 99 |
| 0 | 1 | 8.96 | 0 | 0 |
| 2.24 | 1 | 8.96 | 98 | 50 |
| 4.48 | 1 | 8.96 | 100 | 50 |
| 8.96 | 1 | 8.96 | 100 | 85 |
| 0 | 3 | 8.96 | 0 | 0 |
| 2.24 | 3 | 8.96 | 100 | 40 |
| 4.48 | 3 | 8.96 | 99 | 65 |
| 8.96 | 3 | 8.96 | 100 | 85 |
| 0 | 4 | 8.96 | 0 | 0 |
| 2.24 | 4 | 8.96 | 96 | 45 |
| 4.48 | 4 | 8.96 | 99 | 50 |
| 8.96 | 4 | 8.96 | 100 | 95 |
| 0 | 2 | 8.96 | 0 | 0 |
| 2.24 | 2 | 8.96 | 100 | 70 |
| 4.48 | 2 | 8.96 | 97 | 85 |
| 8.96 | 2 | 8.96 | 100 | 95 |

The above data illustrate that the 5-aryl-4-isothiazolecarboxylic acids of the foregoing formula are effective in reducing herbicidal injury to rice plants.

The safening agents may be applied to the plant locus as a mixture, i.e., a mixture of a herbicidally effective amount of herbicide and a safening effective amount of safening agent, or sequentially, i.e., the plant locus may be treated with an effective amount of the herbicide followed by a treatment with the safening agent or vice versa. The ratio of herbicide to safening agent may vary depending upon the crop to be protected, weeds to be inhibited, herbicide used, etc., but normally a herbicide to safening agent ratio ranging from 1:25 to 25:1 (preferably 1:5 to 5:1) parts by weight may be employed.

The herbicide, safening agent or mixture thereof may be applied to the plant locus alone or the herbicide, safening agent or mixture thereof may be applied in conjunction with a material referred to in the art as an adjuvant in liquid or solid form. Mixtures containing the appropriate herbicide and safening agent usually are prepared by mixing said herbicide and safening agent with an adjuvant including diluents, extenders, carriers and conditioning agents to provide compositions in the form of finely-divided particulate solids, granules, pellets, wettable powders, dusts, solutions and aqueous dispersions or emulsions. Thus, the mixture may include an adjuvant such as a finely-divided particulate solid, a solvent liquid of organic origin, water, a wetting agent, dispersing agent, or emulsifying agent or any suitable combination of these.

When applying the herbicide, safening agent or mixture thereof to the plant locus, useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful include for example, Stoddard solvent, acetone, alcohols, glycols, ethyl acetate, benzene and the like. Such compositions, particularly liquids and wettable powders, usually contain as a conditioning agent one or more surface-active agents in amounts sufficient to render a given composition readily dispersible in water or in oil. By the term "surface-active agent", it is understood that wetting agents, dispersing agents, suspending agents and emulsifying agents are included therein. Such surface-active agents are well known and reference is made to U.S. Pat. No. 2,547,724, Columns 3 and 4, for detailed examples of the same.

Compositions of this invention generally contain from about 5 to 95 parts herbicide and safening agent, about 1 to 50 parts surface-active agent and about 4 to 94 parts solvent, all parts being by weight based on the total weight of the composition.

The application of the herbicide, safening agent or mixture thereof in a liquid or particulate solid form can be carried out by conventional techniques utilizing, for example, spreaders, power dusters, boom and hand sprayers, spray dusters and granular applications. The compositions can also be applied from airplanes as a dust or spray. If desired, application of the compositions of the invention to plants can be accomplished by incorporating the compositions in the soil or other media.

Thus, the present invention encompasses the selective control of undesired vegetation surrounding rice plants by applying butachlor to rice plants that have been treated with the 5-aryl-4-isothiazolecarboxylic acids of the present invention. In this connection, the rice plant locus or the seed of the rice plant may have been previously treated. Additionally, the rice plant locus may be treated with a mixture of butachlor and safening agent.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of safening rice plants against the herbicidal action of butachlor herbicide which comprises treating the rice plant locus with an effective amount of a compound having the formula

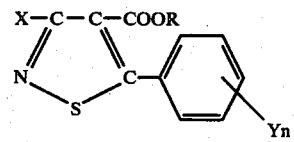

wherein X is hydrogen or chlorine, R is hydrogen, or agriculturally acceptable cations, Y is chlorine or $CF_3$ and n is 0, 1 or 2.

2. A method according to claim 1 wherein X is chlorine.

3. A method according to claim 1 wherein R is hydrogen.

4. A method for selectively controlling the growth of undesirable vegetation surrounding rice plants which comprises treating said rice plant locus with a herbicidally effective amount of butachlor herbicide, said rice plants having been safened against the phytotoxic effects of said herbicide by treatment of said rice plant locus with a compound having the formula

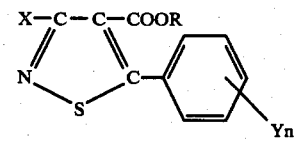

wherein X is hydrogen or chlorine, R is hydrogen, or agriculturally acceptable cations, Y is chlorine or $CF_3$ and n is 0, 1 or 2.

5. A method according to claim 4 wherein R is hydrogen.

6. A method according to claim 4 wherein X is chlorine.

7. A herbicidal mixture comprising a herbicidally effective amount of butachlor herbicide and a safening effective amount of a safening agent having the formula:

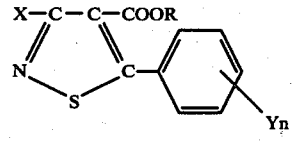

wherein X is hydrogen or chlorine, R is hydrogen lower alkyl or agriculturally acceptable cations, Y is chlorine or $CF_3$ and n is 0, 1 or 2, said herbicide to safening agent ratio ranging from about 1:5 to 5:1.

8. A mixture according to claim 7 wherein R is hydrogen.

9. A mixture according to claim 7 wherein X is chlorine.